United States Patent

Hill et al.

[11] Patent Number: 5,235,082
[45] Date of Patent: Aug. 10, 1993

[54] CATIONIC DIQUATERNARY AMMONIUM SALT FUNCTIONAL SILICONES

[75] Inventors: Randal M. Hill, Midland; Steven A. Snow, Sanford, both of Mich.

[73] Assignee: Dow Corning Corporation, Midland, Mich.

[21] Appl. No.: 2,379

[22] Filed: Jan. 8, 1993

[51] Int. Cl.$^5$ ............................................. C07F 7/10
[52] U.S. Cl. .................................................... 556/425
[58] Field of Search .......................................... 556/425

[56] References Cited

U.S. PATENT DOCUMENTS

| | | | |
|---|---|---|---|
| 4,005,024 | 1/1977 | Rodriguez et al. | 556/425 X |
| 4,417,066 | 11/1983 | Westall | 556/425 |
| 4,833,225 | 5/1989 | Schaefer et al. | 556/425 X |
| 4,891,166 | 1/1990 | Schaefer et al. | 260/404.5 |
| 5,064,543 | 11/1991 | Coffindaffer et al. | 556/425 X |
| 5,064,544 | 11/1991 | Liu et al. | 556/425 X |
| 5,087,715 | 2/1992 | Snow | 556/425 X |

*Primary Examiner*—Paul F. Shaver
*Attorney, Agent, or Firm*—James L. DeCesare

[57] ABSTRACT

Compounds of the formula

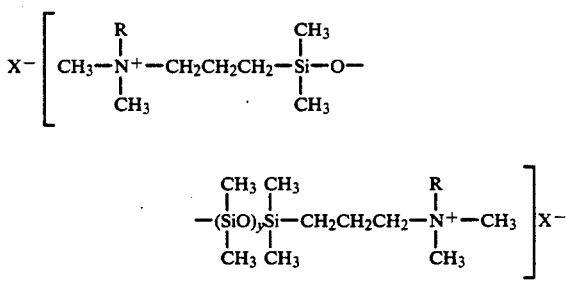

in which R is an alkyl radical having from one to six carbon atoms, a benzyl radical $C_6H_5CH_2$—, or the radical —$(CH_2)_2OH$; $X^-$ is halogen selected from the group consisting of chloride, bromide, and iodide, or $CH_3OSO_3$; and y is an integer having a value of from four to eleven. The compounds have utility as fabric softening and fabric conditioning agents.

5 Claims, No Drawings

CATIONIC DIQUATERNARY AMMONIUM SALT FUNCTIONAL SILICONES

BACKGROUND OF THE INVENTION

This invention is directed to certain silicone compounds which are diquaternary ammonium functional polysiloxanes. The silicone compounds have a variable amount of hydrophobicity at the center of the molecule. The degree of hydrophobicity of the molecule can be adjusted for the purpose of controlling the effectiveness of deposition of the silicone compound on fabrics, thereby rendering these compounds more useful in the field of fabric softening and fabric conditioning. The adjustable molecular center makes it possible to tailor compounds with more desirable hydrophile/lipophile balances for aqueous applications such as fabric softening and fabric conditioning.

Diquaternary polysiloxanes are known in the art. For example, in U.S. Pat. No. 4,891,166 issued Jan. 2, 1990, there are described products which are said to be useful in preparations for the care of the hair. While the compounds of the '166 patent are diquaternary silicones, they differ significantly from the compounds of the present invention in that a linking group "M" between the silicon atom and the quaternary ammonium group "Z" requires the presence of a hydroxyl group and which may be interrupted by an oxygen atom. An example of a typical linking group "M" of the '166 patent is $-(CH_2)_3OCH_2CH(OH)CH_2-$.

No such linking group is present or necessary in the compounds of the present invention. In addition, at least one of the alkyl radicals $R^1$, $R^2$, and $R^3$, in the '166 patent, which are attached to the positively charged nitrogen atom, is required to contain a minimum of ten carbon atoms; whereas the corresponding alkyl groups of the compounds of the present invention do not exceed six. Such differences cause the compounds of the '166 patent to possess deposition properties inappropriate for fabric conditioning and softening applications.

SUMMARY OF THE INVENTION

The invention relates to compounds of the formula

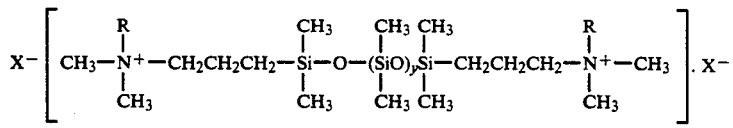

By changing the value of the integer "y", the length of the siloxane chain can be varied for the purpose of adjusting the degree of hydrophobicity of the molecule. This will increase the effectiveness of control of the deposition of the compound with respect to laundry fabric. With controllable deposition properties, the compounds have utility in softening and conditioning applications in commercial laundry detergent/softening formulations. The compounds also offer the advantage of possessing a lower critical micelle concentration with the result that they can be effectively adsorbed at lower concentrations. Cost savings in the commercial laundry detergent market is a significant benefit in both wash cycle and rinse cycle products.

These and other features, objects, and advantages, of the herein described present invention, will become more apparent from a consideration of the following detailed description thereof.

DETAILED DESCRIPTION OF THE INVENTION

The compounds of the present invention can be characterized as alpha-omega or bolaform surfactant materials possessing a polar group on each end of a linear chain. As noted above, the compounds have the formula

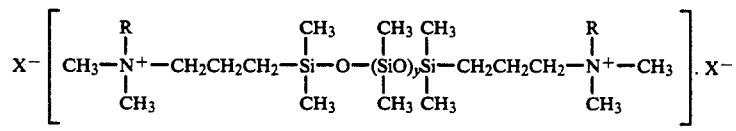

In the above formula, R is an alkyl radical having from one to six carbon atoms; a benzyl radical $C_6H_5CH_2-$; or the radical $-(CH_2)_2OH$. Preferably, R is methyl. The counterion $X^-$ is halogen such as chloride, bromide, and iodide; or $CH_3OSO_3$. The value of the integer "y" in the formula may vary from four to eleven.

The compounds may be prepared by one of two methods. In the first method of preparation, N,N-dimethylallylamine $H_2C=CHCH_2NMe_2$ is hydrosilylated with an Si—H functional endblocked siloxane, followed by the quaternization of the tertiary amine product with methyl iodide MeI or benzyl chloride $C_6H_5CH_2Cl$. In the other method of preparation, vinyl benzyl chloride $H_2C=CHC_6H_4CH_2Cl$ is hydrosilylated with an Si—H functional endblocked siloxane, followed by the quaternization of the benzyl chloride functional siloxane with dimethylethanolamine $Me_2N(CH_2)_2OH$.

The two methods for the preparation of the compounds of the present invention are set forth in the equations set forth below. Equation I demonstrates the synthesis of a tertiary amine endblocked siloxane from an Si-H functional endblocked precursor.

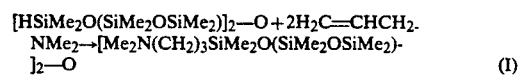

(I)

Once the tertiary amine enblocked siloxane is synthesized, it is directly quaternized with methyl iodide or benzyl chloride. Quaternization with methyl iodide is shown in Equation II.

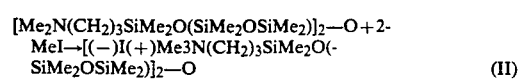

(II)

Quaternization with benzyl chloride is shown in Equayion III.

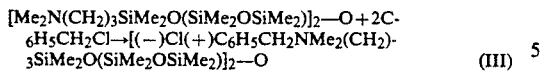
$$[Me_2N(CH_2)_3SiMe_2O(SiMe_2OSiMe_2)]_2-O + 2C_6H_5CH_2Cl \rightarrow [(-)Cl(+)C_6H_5CH_2NMe_2(CH_2)_3SiMe_2O(SiMe_2OSiMe_2)]_2-O \quad (III)$$

While Equations II and III show the use of methyl iodide and benzyl chloride, other alkylating agents such as methyl chloride, methyl bromide, dimethyl sulfate, and ethyl bromide, may be used to alkylate the tertiary amine functional siloxane under mild conditions.

The other method of making the quaternary salt functional siloxanes of the present invention involves the quaternization of benzyl chloride functional siloxanes. This method is set forth in the Equation IV below.

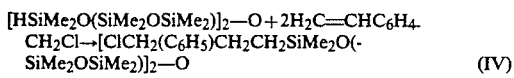
$$[HSiMe_2O(SiMe_2OSiMe_2)]_2-O + 2H_2C=CHC_6H_4-CH_2Cl \rightarrow [ClCH_2(C_6H_5)CH_2CH_2SiMe_2O(SiMe_2OSiMe_2)]_2-O \quad (IV)$$

The quaternization of the benzyl chloride functional siloxane with dimethylethanolamine is shown in Equation V.

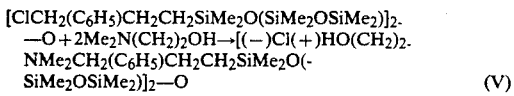
$$[ClCH_2(C_6H_5)CH_2CH_2SiMe_2O(SiMe_2OSiMe_2)]_2-O + 2Me_2N(CH_2)_2OH \rightarrow [(-)Cl(+)HO(CH_2)_2NMe_2CH_2(C_6H_5)CH_2CH_2SiMe_2O(SiMe_2OSiMe_2)]_2-O \quad (V)$$

Other tertiary amines may be used to quaternize the benzyl chloride functional siloxane in Equation V other than dimethylethanolamine as illustrated under mild conditions.

The compounds of the present invention were characterized by proton nuclear magnetic resonance, mass, and (NMR) and infrared (IR) spectroscopies. Routine proton NMR spectra were obtained on a Varian EM3-60A instrument operating at sixty MHz. Electron impact GC/MS data was obtained on a Hewlett-Packard 5971A MSD at seventy eV. IR spectra were collected on a Perkin-Elmer 1710FT-IR Spectrometer. GC analyses were performed on a Hewlett-Packard 5890 Gas Chromatograph using a twelve meter fused capillary column with flame ionization detection (FID).

The following examples are set forth for the purpose of further illustrating the concepts of the present invention.

EXAMPLE I

Preparation of
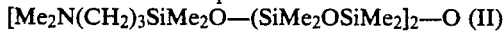
$[Me_2N(CH_2)_3SiMe_2O-(SiMe_2OSiMe_2]_2-O$ (II)

50.0 g (116 mmol) of a polydimethylsiloxane having a degree of polymerization of six and endblocked with Si—H, was heated to 100 degree C. under inert atmosphere. To this was first added 4 drops of 0.1M H₂PtCl₆ in IPA (catalyst), then 16.9 g (119 mmol) of N,N-dimethylallylamine at a rate of approximately 1 drop/sec. The temperature was maintained at 90–100 degrees C. for 6 hours. At this point 4 more drops of the catalyst was added, and the temperature of the mixture was maintained at 105 degrees C. for 2 hours. A GC analysis indicated complete consumption of the reactants primarily to a single product (II). The crude product was filtered through Fuller's Earth and activated carbon. The resultant clear solution was stripped in vacuo to a maximum condition of 100 degrees C., 1 mm Hg pressure. The structure of the product was confirmed by proton NMR and IR spectroscopic data. The above synthesis procedure was repeated using an Si—H endblocked polydimethylsiloxane fluid having a degree of polymerization of thirteen.

EXAMPLE II

Preparation of [I(−)
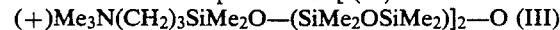
$(+)Me_3N(CH_2)_3SiMe_2O-(SiMe_2OSiMe_2)]_2-O$ (III)

20.2 g (34 mmol) of II was mixed with 100 ml of toluene under inert atmosphere and the mixture was heated to 45 degrees C. 11.5 g (81 mmol) of iodomethane was added dropwise to the above mixture. This addition resulted in the formation of a thick, viscous gel which was taken up into 100 ml of methanol. The resultant solution was stripped in vacuo to a maximum condition of 70 degrees C. 40 mm Hg pressure. The product (III) was purified by recrystallization from warm methyl ethyl ketone. The molecular structure of III was confirmed by proton NMR and IR spectroscopies.

EXAMPLE III

Preparation of [Cl(−)
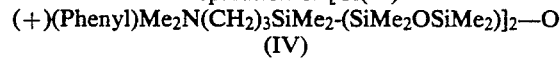
$(+)(Phenyl)Me_2N(CH_2)_3SiMe_2-(SiMe_2OSiMe_2)]_2-O$ (IV)

20.8 g (33.5 mmol) of II was mixed under inert atmosphere with 50 g of toluene, and heated to 45 degrees C. 9.3 g (74 mmol) of benzyl chloride was added at a rate of approximately 1 drop/sec to the above solution while the temperature was maintained at 45 degrees C. The mixture was heated to 70 degrees C. and held at that temperature overnight. It was then taken up into methanol and stripped in vacuo to a maximum condition of 100 degrees C., 15 mm Hg pressure. The structure of the resultant solid product (IV) was confirmed by NMR spectroscopy.

EXAMPLE IV

Preparation of
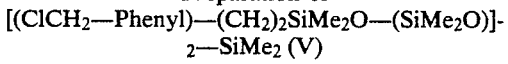
$[(ClCH_2-Phenyl)-(CH_2)_2SiMe_2O-(SiMe_2O)]_2-SiMe_2$ (V)

A mixture of 30.3 g (71 mmol) of Si—H endblocked polydimethylsiloxane fluid having a degree of polymerization of six, and 50 g of toluene was heated to 100 degrees C. under inert atmosphere. Seven drops of 0.1M H₂PtCl₆ in IPA (catalyst), and 23.7 g (155 mmol) of vinyl benzyl chloride (VBC) were added to the solution at a rate of approximately 1 drop/sec. As the reaction progressed, the rate of addition of VBC was slowed to 1 drop/4 sec in order to maintain a temperature of 110 degrees C. After the addition of VBC was completed, the temperature of the mixture was maintained at 100 degrees C. for 30 minutes. The resultant solution was filtered through Fuller's Earth and activated carbon and stripped in vacuo to a maximum condition of 80 degrees C., 2 mm Hg pressure, yielding a liquid product (V). The above hydrosilylation reaction was repeated using an Si-H endblocked polydimethylsiloxane having a degree of polmerization of thirteen.

EXAMPLE V

Preparation of [Cl(−) (+)
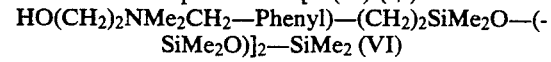
$HO(CH_2)_2NMe_2CH_2-Phenyl)-(CH_2)_2SiMe_2O-(SiMe_2O)]_2-SiMe_2$ (VI)

11.5 g (16 mmol) of V and 50 g of ethylene glycol butyl ether solvent were mixed together under inert atmosphere and heated to 40 degrees C. 3.1 g (34 mmol) of N,N-dimethylethanolamine was added to the above mixture at the rate of 1 drop/sec. The temperature of the resultant mixture was maintained at 40–45 degrees C. for 3 hours, then stripped in vacuo to a maximum condition of 100 degrees C., 2 mm Hg pressure. This quaternization reaction was repeated with a benzyl chloride functional, endblocked polydimethylsiloxane having a degree of polymerization of thirteen.

In Example II, R is methyl; X is chloride; and y is four. In Example III, R is benzyl; X is chloride; and y is four. In Example V, R is —CH$_2$CH$_2$OH; X is chloride; and y is six, for one of the products. For the other product of Example V, R is benzyl; X is chloride; and y is eleven.

The critical micelle concentration of the compound produced in accordance with Example II was determined to be about 0.0001 mol/kg, which is an exceptionally low value for a cationic surfactant, indicating that this compound is very surface active. In addition, the compound of Example II was found to reduce the surface tension of water to 22–23 dynes/cm, again indicating the high surface activity of the compounds of the present invention.

Other variations and modifications may be made in the compounds and methods described herein without departing from the essential features and concepts of the present invention. The forms of the invention described herein are exemplary only and are not intended as limitations on the scope of the invention as defined in the appended claims.

That which is claimed is:

1. A compound having the formula

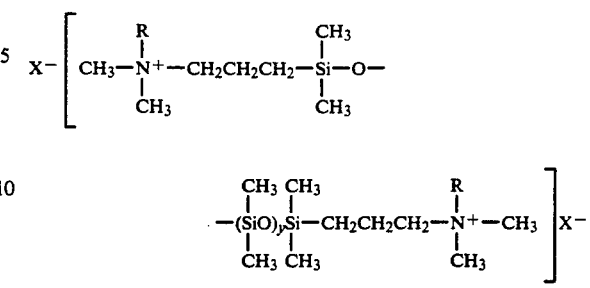

in which R is an alkyl radical having from one to six carbon atoms, a benzyl radical C$_6$H$_5$CH$_2$—, or the radical —(CH$_2$)$_2$OH; X$^-$ is halogen selected from the group consisting of chloride, bromide, and iodide, or CH$_3$O-SO$_3$; and y is an integer having a value of from four to eleven.

2. A compound according to claim 1 in which R is methyl; X is chloride; and y is four.

3. A compound according to claim 1 in which R is benzyl; X is chloride; and y is four.

4. A compound according to claim 1 in which R is —CH$_2$CH$_2$OH; X is chloride; and y is six.

5. A compound according to claim 1 in which R is benzyl; X is chloride; and y is eleven.

* * * * *